April 18, 1933. E. P. WRAY Plant Pat. 61

APPLE

Filed Dec. 9, 1931

INVENTOR
EDWIN P. WRAY
BY
Richards & Geier
ATTORNEYS

Patented Apr. 18, 1933

Plant Pat. 61

UNITED STATES PATENT OFFICE

EDWIN P. WRAY, OF WHITE SALMON, WASHINGTON

APPLE

Application filed December 9, 1931. Serial No. 579,889.

This invention relates to improvements in fruits and has particular reference to an asexually propagated apple.

An object of the invention is to produce a new and distinct variety of apple of unusual contour combined with a uniqueness of color effects which impart a highly esthetic apearance thereto and, further, to produce an apple of hardy growth which will thrive under the climatic and soil conditions ordinarily existent in localities where apples are grown.

The accompanying drawing illustrates the shape and color of the improved apple as closely as it is possible to do artificially and, in this connection, it is to be understood that various minor changes in the characteristic features of the apple may be accomplished without departing from the spirit or scope of the invention as defined by the appended claim.

In the drawing—

Figure 1:
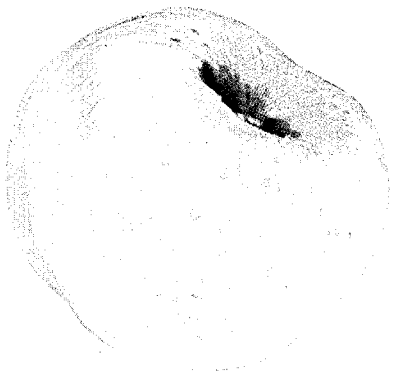
Figure 1 is an elevation of the apple tilted so as to partially expose the stem cavity thereof.
Figure 3:
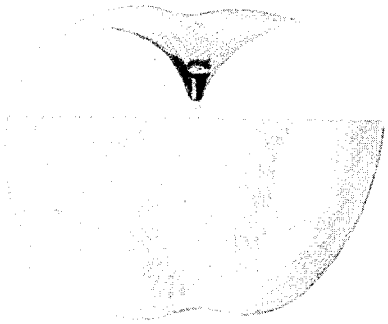
Figure 3 is an elevation, partly cut away, illustrating the stem cavity in section.
Figure 2:
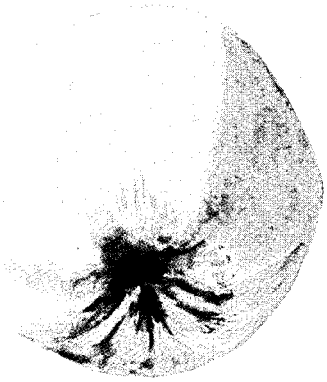
Figure 2 is also an elevation partially turned about its stem axis to show the opposite side of the apple from that illustrated in Figure 1 and tilted to expose the calyx.

Specifically, the characteristic features of the apple, which combine to distinguish the same from other known varieties, comprise an exceptionally deep stem cavity and unusually short stem, and the formation of five points or protuberances of more or less irregular shape and size disposed circumferentially about the calyx.

As to the unique color of the apple, the same is essentially a bright red of varied hue on a yellow background, with the lighter red on the shaded side marked with occasional streaks of a darker red. Numerous small dots appear over practically the entire surface of the apple, these dots being yellow in the darker red areas and having a greenish yellow tint in the lighter portions. In the stem cavity and around the calyx, the color is predominantly green with an occasional small light yellow area, principally in and about the stem cavity.

The present variety of apple was originated by intercrossing the varieties known as the Delicious and the Newton Pippin, using the latter as the pollen parent, and the hybrid resulting from this crossing has been asexually reproduced. The resultant product has a flavor which partakes of the qualities of both varieties and is a late keeper, the same remaining in good condition as late as March under ordinary storage conditions.

The tree from which the apple is obtained is an upright, stocky grower and the leaves thereof have irregularly serrated edges resembling those of the Newton Pippin tree.

What is claimed is:

An apple substantially as herein shown and described, characterized by an exceptionally deep stem cavity and short stem, and five points of more or less irregular formation disposed circumferentially about its calyx, the color of the apple being a varicolored red on a yellow background, with the area of lighter red having slight markings of a darker red, and substantially the entire area of the apple being flecked with small dots, the dots in the darker red portion being yellow and those in the lighter area being of a greenish yellow tint.

In testimony whereof, I have affixed my signature.

EDWIN P. WRAY.